US00PP34057P2

(12) United States Plant Patent
Yao et al.

(10) Patent No.: US PP34,057 P2
(45) Date of Patent: Mar. 22, 2022

(54) ***NELUMBO* PLANT NAMED 'ZHONGSHAN CHANYUN'**

(50) Latin Name: *Nelumbo nucifera*
Varietal Denomination: Zhongshan Chanyun

(71) Applicants: Dongrui Yao, Nanjing (CN); Xiaojing Liu, Nanjing (CN); Fengfeng Du, Nanjing (CN); Linhe Sun, Nanjing (CN); Jinfeng Li, Nanjing (CN)

(72) Inventors: Dongrui Yao, Nanjing (CN); Xiaojing Liu, Nanjing (CN); Fengfeng Du, Nanjing (CN); Linhe Sun, Nanjing (CN); Jinfeng Li, Nanjing (CN)

(73) Assignees: INSTITUTE OF BOTANY, Jiangsu Province (CN); CHINESE ACADEMY OF SCIENCE, Nanjing (CN)

( * ) Notice: Subject to any disclaimer, the term of this patent is extended or adjusted under 35 U.S.C. 154(b) by 0 days.

(21) Appl. No.: 17/149,651

(22) Filed: Jan. 14, 2021

(51) Int. Cl.
*A01H 5/02* (2018.01)
*A01H 6/00* (2018.01)

(52) U.S. Cl.
USPC ..... Plt./342

(58) Field of Classification Search
USPC ..... Plt./342
See application file for complete search history.

*Primary Examiner* — Annette H Para
(74) *Attorney, Agent, or Firm* — C. Anne Whealy

(57) ABSTRACT

A new and distinct cultivar of *Nelumbo* plant named 'Zhongshan Chanyun', characterized by its upright to somewhat outwardly spreading plant habit; vigorous growth habit; large dark green-colored leaves; freely flowering habit; large purplish pink-colored ball-shaped flowers with numerous petals and petaloids; flowers that are positioned above the foliar plane on moderately strong and erect peduncles; good garden performance and good postproduction longevity.

3 Drawing Sheets

Figure 1:
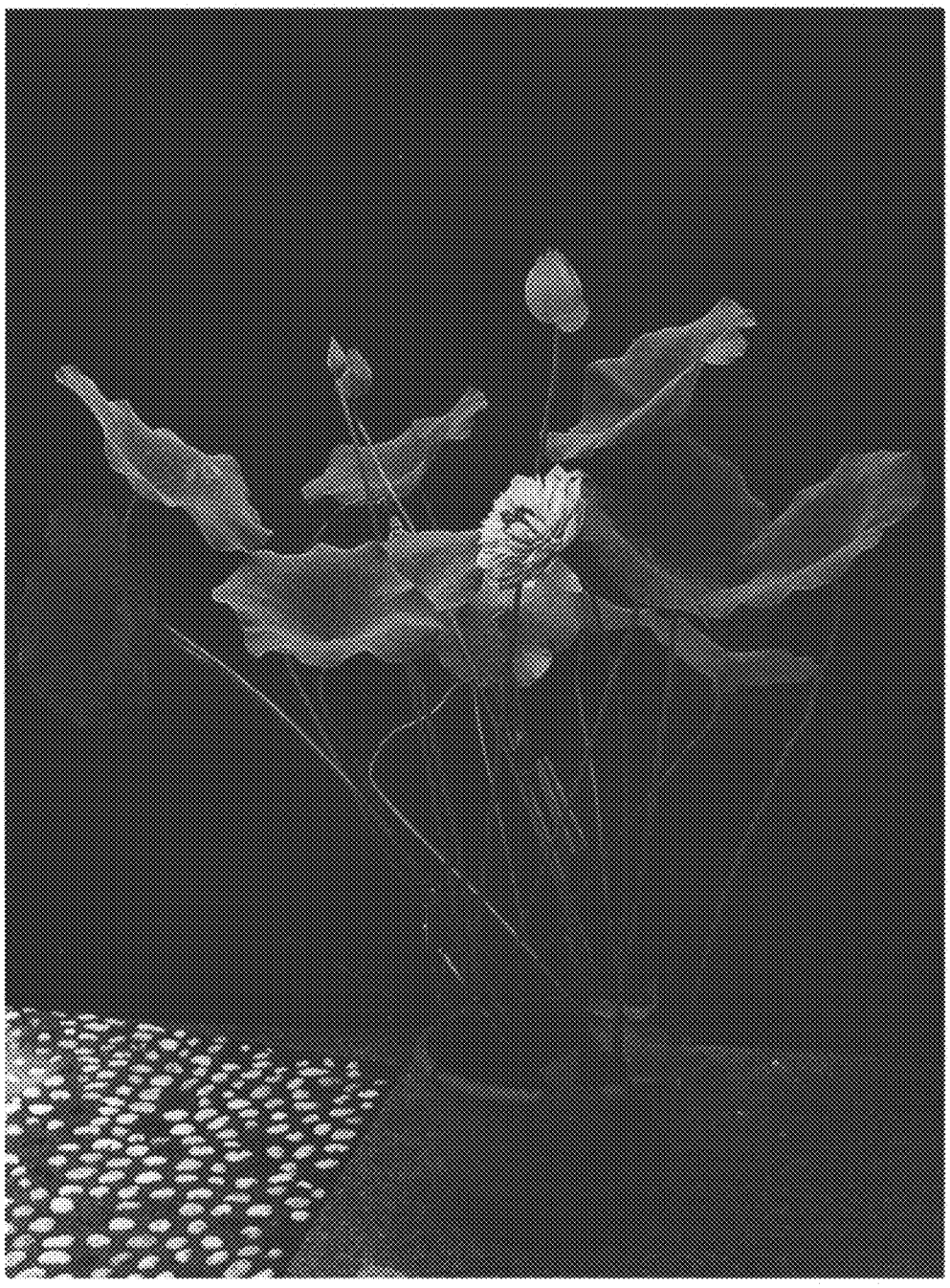

Botanical designation: *Nelumbo nucifera.*
Cultivar denomination: 'Zhongshan Chanyun'.

BACKGROUND OF THE INVENTION

The present invention relates to a new and distinct cultivar of *Nelumbo* plant, botanically known as *Nelumbo nucifera*, commonly referred to as Sacred or Indian Lotus, and hereinafter referred to by the name 'Zhongshan Chanyun'.

The new *Nelumbo* plant is a product of a controlled breeding program conducted by the Inventors in Nanjing, Jiangsu Province, China. The objective of the breeding program is to create new *Nelumbo* plants that have large double-type flowers with numerous petals and petaloids with attractive coloration.

The new *Nelumbo* plant originated from a cross-pollination in July, 2017 of *Nelumbo nucifera* 'Xiao Lianzuo', not patented, as the female, or seed, parent with *Nelumbo nucifera* 'Xiuqiu', not patented, as the male, or pollen, parent. The new *Nelumbo* plant was discovered and selected by the Inventors as a single flowering plant within the progeny of the stated cross-pollination in a controlled greenhouse environment in Nanjing, Jiangsu Province, China in June, 2018.

Asexual reproduction of the new *Nelumbo* plant by rhizome divisions in a controlled environment in Nanjing, Jiangsu Province, China since March, 2019 has shown that the unique features of this new *Nelumbo* plant are stable and reproduced true to type in successive generations of asexual reproduction.

SUMMARY OF THE INVENTION

Plants of the new *Nelumbo* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Zhongshan Chanyun'. These characteristics in combination distinguish 'Zhongshan Chanyun' as a new and distinct *Nelumbo* plant:

1. Upright to somewhat outwardly spreading plant habit.
2. Vigorous growth habit.
3. Large dark green-colored leaves.
4. Freely flowering habit.
5. Large purplish pink-colored ball-shaped flowers with numerous petals and petaloids.
6. Flowers are positioned above the foliar plane on moderately strong and erect peduncles.
7. Good garden performance and good postproduction longevity; plants are suitable as garden plants, potted plants and as cut flowers.

Plants of the new *Nelumbo* differ from plants of the female parent, 'Xiao Lianzuo', in the following characteristics:

1. Flowers of plants of the new *Nelumbo* are ball-shaped whereas flowers of plants of 'Xiao Lianzuo' are bowl-shaped.
2. Flowers of plants of the new *Nelumbo* have twice as many petals than flowers of plants of 'Xiao Lianzuo'.
3. Stamens of flowers of plants of the new *Nelumbo* are all transformed into petaloids whereas most of the stamens of flowers of plants of 'Xiao Lianzuo' are not transformed into petaloids.
4. Flowers of plants of the new *Nelumbo* do not produce seeds whereas flowers of plants of 'Xiao Lianzuo' produce seeds.

5. Flowers of plants of the new *Nelumbo* have good postproduction longevity and can be used as cut flowers whereas flowers of plants of 'Xiao Lianzuo' are short-lived and not suitable for use as cut flowers.

Plants of the new *Nelumbo* differ from plants of the male parent, 'Xiuqiu', in the following characteristics:

1. Flowers of plants of the new *Nelumbo* are ball-shaped whereas flowers of plants of 'Xiuqiu' are plate-shaped.
2. Flowers of plants of the new *Nelumbo* have many more petals than flowers of plants of 'Xiuqiu'.
3. Stamens of flowers of plants of the new *Nelumbo* are all transformed into petaloids whereas most of the stamens of flowers of plants of 'Xiuqiu' are not transformed into petaloids.
4. Flowers of plants of the new *Nelumbo* do not produce seeds whereas flowers of plants of 'Xiuqiu' produce seeds.
5. Flowers of plants of the new *Nelumbo* have good postproduction longevity and can be used as cut flowers whereas flowers of plants of 'Xiuqiu' are short-lived and not suitable for use as cut flowers.

Plants of the new *Nelumbo* can be compared to plants of *Nelumbo nucifera* 'Taoliu Yiyi', not patented. In side-by-side comparisons plants of the new *Nelumbo* differ primarily from plants of 'Taoliu Yiyi', in the following characteristics:

1. Flowers of plants of the new *Nelumbo* are ball-shaped whereas flowers of plants of 'Taoliu Yiyi' are bowl-shaped.
2. Flowers of plants of the new *Nelumbo* have many more petals than flowers of plants of 'Taoliu Yiyi'.
3. Stamens of flowers of plants of the new *Nelumbo* are all transformed into petaloids whereas most of the stamens of flowers of plants of 'Taoliu Yiyi' are not all transformed into petaloids.
4. Flowers of plants of the new *Nelumbo* have good postproduction longevity and can be used as cut flowers whereas flowers of plants of 'Taoliu Yiyi' are short-lived and not suitable for use as cut flowers.

BRIEF DESCRIPTION OF THE PHOTOGRAPHS

The accompanying photographs illustrate the overall appearance of the new *Nelumbo* plant showing the colors as true as it is reasonably possible to obtain in colored reproductions of this type. Colors in the photographs may differ slightly from the color values cited in the detailed botanical description which accurately describe the colors of the new *Nelumbo* plant.

The photograph on the first sheet (FIG. 1) is a side perspective view of a typical plant of 'Zhongshan Chanyun' grown in a container.

Figure 2:
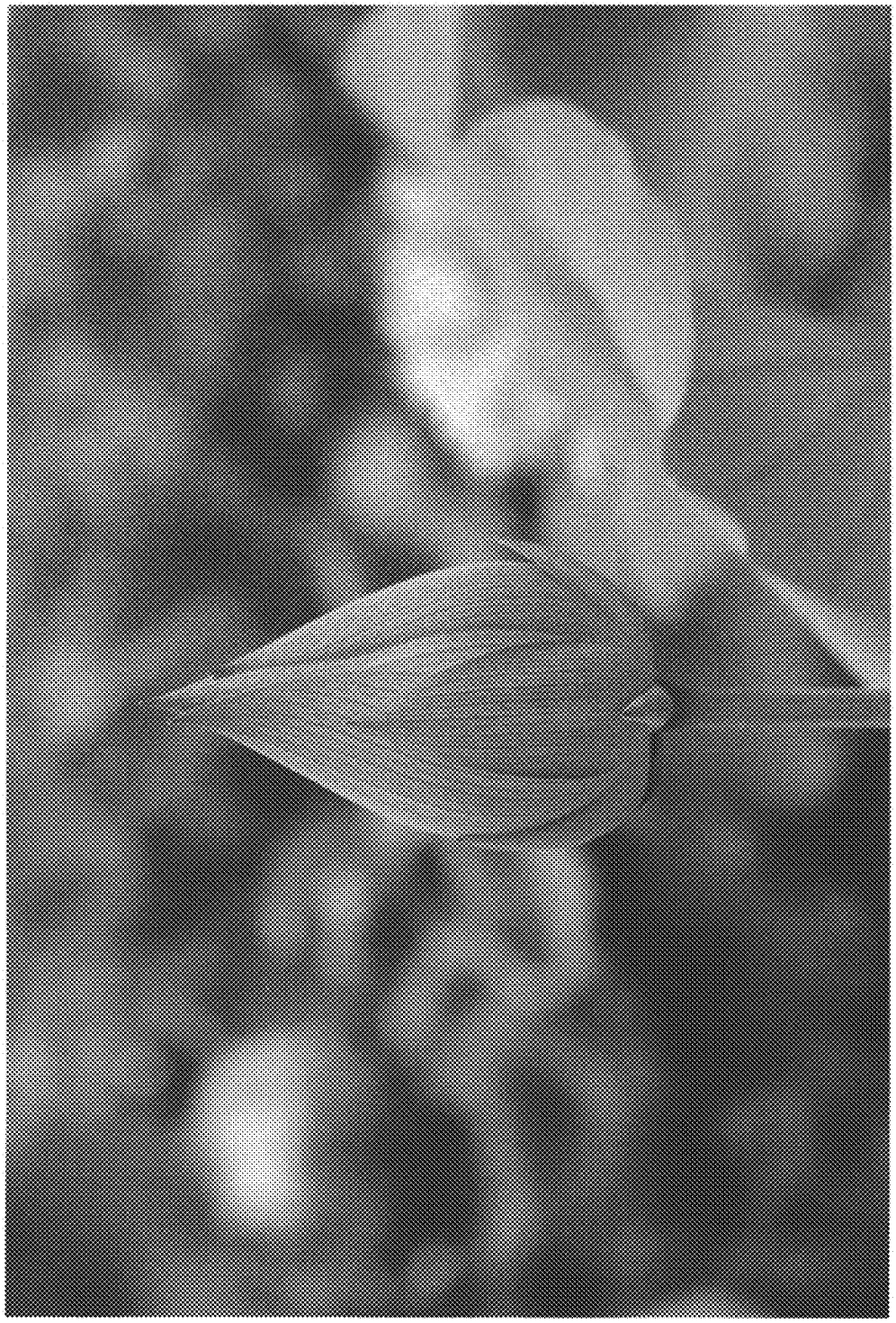

The photograph on the second sheet (FIG. 2) is a close-up view of a typical flower bud of 'Zhongshan Chanyun'.

Figure 3:
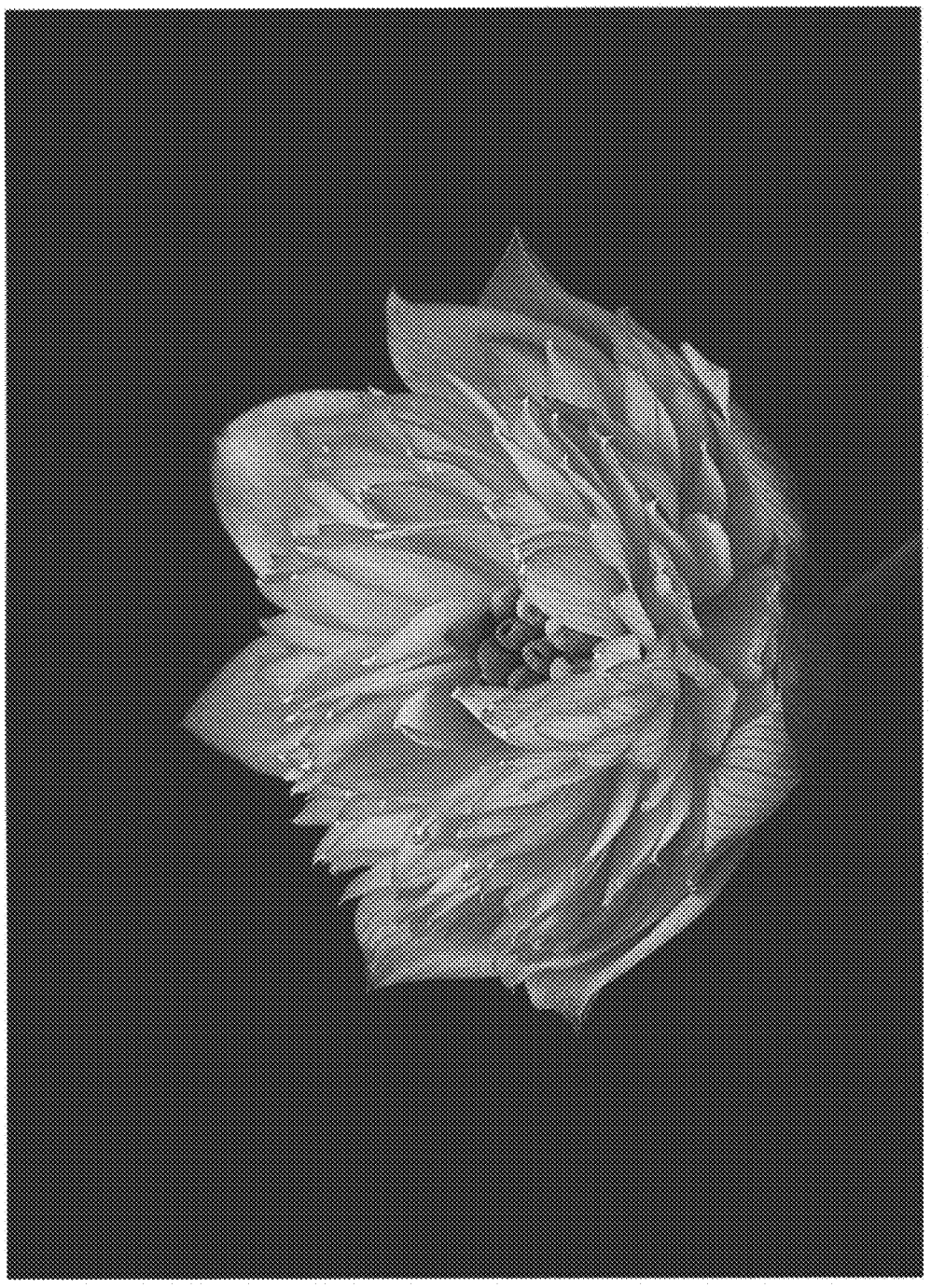

The photograph on the third sheet (FIG. 3) is a close-up view of a typical flower of 'Zhongshan Chanyun'.

DETAILED BOTANICAL DESCRIPTION

The aforementioned photographs and following observations and measurements describe plants grown during the summer in 38-cm by 35-cm containers in an outdoor nursery in Nanjing, Jiangsu Province, China and under cultural practices typical of commercial *Nelumbo* production. During the production of the plants, day temperatures ranged from 25° C. to 38° C. and night temperatures ranged from 20° C. to 30° C. Plants were one year old when the photographs and the detailed description were taken. In the following description, color references are made to The Royal Horticultural Society Colour Chart, 2015 Edition, except where general terms of ordinary dictionary significance are used.

Botanical classification: *Nelumbo nucifera* 'Zhongshan Chanyun'.

Parentage:

*Female, or seed, parent.*—*Nelumbo nucifera* 'Xiao Lianzuo', not patented.

*Male, or pollen, parent.*—*Nelumbo nucifera* 'Xiuqiu', not patented.

Propagation:

*Type.*—By rhizome divisions.

*Time to initiate roots, summer.*—About three to four days at temperatures about 27° C.

*Time to produce a rooted young plant, summer.*—About seven days at temperatures about 27° C.

*Rhizome length.*—About 6.8 cm.

*Rhizome diameter.*—About 1.2 cm.

*Rhizome shape.*—Cylindrical, nodose.

*Rhizome texture and luster.*—Fleshy, smooth; matte.

*Rhizome color.*—Typically creamy white to yellowish brown in color, actual color of the rhizomes is dependent on water quality, fertilizer type and formulation, substrate temperature and physiological age of roots.

Plant description:

*Plant and growth habit.*—Upright to somewhat outwardly spreading plant habit; vigorous growth habit and moderate growth rate.

*Plant height* (*soil level to top of foliar plane*).—About 97.5 cm.

*Plant height* (*soil level to top of floral plane*).—About 105 cm.

*Plant diameter.*—About 78 cm by 90 cm.

Leaf description:

*Length, fully expanded.*—About 30.3 cm.

*Width, fully expanded.*—About 24.1 cm.

*Shape.*—Peltate, orbicular; petiole attached to the center of the leaf.

*Apex.*—Retuse.

*Margin.*—Entire; slightly undulate.

*Venation.*—Radiating from the center; reticulate.

*Texture and luster, upper surface.*—Smooth, glabrous; matte.

*Texture and luster, lower surface.*—Cancellate, glabrous; matte.

*Color.*—Developing leaves, upper surface: Close to 137B. Developing leaves, lower surface: Close to 138C. Fully expanded leaves, upper surface: Close to NN137A; venation, close to 136D. Fully expanded leaves, lower surface: Close to 138A; venation, close to 143C.

*Petioles.*—Length: About 95 cm. Diameter: About 7 mm. Strength: Moderately strong. Texture and luster, upper and lower surfaces: Smooth, glabrous; slightly glossy. Color, upper and lower surfaces: Close to 146C.

Flower description:

*Arrangement.*—Double-type ball-shaped flowers developing directly from the rhizomes with numerous showy petals and petaloids; about six flower buds and flowers developing per plant at one time; flowers face mostly upright.

*Time to flower*.—In China, plants flower continuously during the summer.

*Flower longevity*.—Flowers last about 60 days on the plant and flowers last about one weeks a cut flower; flowers not persistent.

*Fragrance*.—Moderately fragrant; pleasant.

*Flower buds*.—Length: About 8.3 cm. Diameter: About 5.6 cm. Shape: Broadly ovate. Texture and luster: Glabrous; matte. Color: Petals, close to 62B with venation, close to 64B; sepals, close to 144A with venation, close to 64B.

*Flower shape and arrangement*.—Double-type, ball-shaped with numerous showy petals and petaloids.

*Flower diameter*.—About 14.6 cm by 14.4 cm.

*Flower height*.—About 7.2 cm.

*Petals*.—Quantity and arrangement: About 215 arranged in about eight whorls. Length: About 8.2 cm. Width: About 4.3 cm. Shape: Ovoid. Apex: Mucronulate. Base: Truncate. Margins: Entire; slightly undulate. Texture and luster, upper surface: Smooth, glabrous; papery; slightly glossy. Texture and luster, lower surface: Slightly rugose, glabrous; papery; very slightly glossy. Color: When opening, upper surface: Center, close to 62B, towards the apex, close to 59C, and towards the base, close to 1C. When opening, lower surface: Center, close to 62B, towards the apex, close to 59C, and towards the base, close to 1D. Fully opened, upper surface: Center, close to 63D, towards the apex, close to 60B, and towards the base, close to 1D; venation, close to 63B; with development, center becoming closer to 62C, towards the apex, close to 61B, and towards the base, close to 2D. Fully opened, lower surface: Center, close to 63D, towards the apex, close to 60B, and towards the base, close to 2D; venation, close to 64B; with development, center becoming closer to 62D, towards the apex, close to 61B, and towards the base, close to 2D.

*Petaloids*.—Quantity and arrangement: About 202 arranged in numerous whorls. Length: About 6.7 cm. Width: About 1.4 cm. Shape: Obovate to lanceolate. Apex: Mucronulate. Base: Cuneate. Margins: Entire; not undulate. Texture and luster, upper surface: Smooth, glabrous; papery; slightly glossy. Texture and luster, lower surface: Slightly rugose, glabrous; papery; very slightly glossy. Color: When opening, upper surface: Close to N66D and towards the base, close to 1C. When opening, lower surface: Close to 63C and towards the base, close to 1D. Fully opened, upper surface: Close to 63C and towards the base, close to 1D; venation, close to 64C; with development, color becoming closer to 63D and towards the base, close to 2D. Fully opened, lower surface: Close to 62B and towards the base, close to 2D; venation, close to 67B; with development, color becoming closer to 62C and towards the base, close to 2D.

*Sepals*.—Quantity and arrangement: Four in a single whorl. Length: About 2.6 cm. Width: About 1.1 cm. Shape: Ovoid. Apex: Mucronulate. Base: Truncate. Margin: Entire. Texture and luster, upper and lower surfaces: Smooth, glabrous; papery; slightly glossy. Color: When opening, upper surface: Close to 183C and towards the base, close to 144B. When opening, lower surface: Close to 144A and towards the apex, close to 183C. Fully opened, upper surface: Close to 155A and towards the apex, close to 59B. Fully opened, lower surface: Close to 144B and towards the apex, close to 59B.

*Peduncles*.—Length: About 99 cm. Diameter: About 6 mm. Strength: Moderately strong. Aspect: Mostly erect to outwardly leaning. Texture and luster, upper and lower surfaces: Smooth, glabrous; slightly glossy. Color, upper and lower surfaces: Close to 146C.

*Stamens*.—Stamens are all transformed into petaloids; to date, no stamen development has been observed on plants of the new *Nelumbo*.

*Pistils*.—To date, pistil development has not been observed on plants of the new *Nelumbo*.

*Fruits and seeds*.—To date, fruit and seed development has not been observed on plants of the new *Nelumbo*.

Pathogen & pest resistance: To date, plants of the new *Nelumbo* have not been observed to be resistant to pathogens or pests common to *Nelumbo* plants.

Temperature tolerance: Plants of the new *Nelumbo* have been observed to be tolerant to temperatures ranging from about −10° C. to about 40° C. and to be suitable for USDA Hardiness Zones 6a to 13b.

It is claimed:

1. A new and distinct *Nelumbo* plant named 'Zhongshan Chanyun' as illustrated and described.

* * * * *